United States Patent
Zdeblick

(10) Patent No.: US 8,412,347 B2
(45) Date of Patent: Apr. 2, 2013

(54) METHODS AND APPARATUS FOR LEADS FOR IMPLANTABLE DEVICES

(75) Inventor: Mark Zdeblick, Portola Valley, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 526 days.

(21) Appl. No.: 12/514,045

(22) PCT Filed: Apr. 29, 2009

(86) PCT No.: PCT/US2009/042147
§ 371 (c)(1),
(2), (4) Date: May 7, 2009

(87) PCT Pub. No.: WO2010/126503
PCT Pub. Date: Nov. 4, 2010

(65) Prior Publication Data
US 2010/0318163 A1    Dec. 16, 2010

(51) Int. Cl.
*A61N 1/00*    (2006.01)
(52) U.S. Cl. ............ 607/115; 607/9; 607/36; 607/37
(58) Field of Classification Search ............ 607/9, 115, 607/36–37
See application file for complete search history.

(56) References Cited

U.S. PATENT DOCUMENTS

| | | |
|---|---|---|
| 2,956,586 A | 10/1960 | Zeigler et al. |
| 3,888,260 A | 6/1975 | Fischell |
| 3,985,123 A | 10/1976 | Herzlinger et al. |
| 4,164,946 A | 8/1979 | Langer |
| 4,262,982 A | 4/1981 | Kenny |
| 4,397,314 A | 8/1983 | Vaguine |
| 4,399,820 A | 8/1983 | Wirtzfeld et al. |
| 4,600,454 A | 7/1986 | Plummer |
| 4,603,705 A | 8/1986 | Speicher et al. |
| 4,628,934 A | 12/1986 | Pohndorf et al. |
| 4,628,935 A | 12/1986 | Jones et al. |
| 4,750,494 A | 6/1988 | King |
| 4,776,334 A | 10/1988 | Prionas |

(Continued)

FOREIGN PATENT DOCUMENTS

| | | |
|---|---|---|
| EP | 0659388 | 6/1995 |
| EP | 1050265 | 11/2000 |

(Continued)

OTHER PUBLICATIONS

U.S. Appl. No. 11/917,992, filed on Jul. 13, 2009 (Specification, Claims, Abstract and Figures as filed); Jensen et al., (2009) "Deployable Epicardial Electrode and Sensor Array" 69pp.

(Continued)

*Primary Examiner* — Nicole F Lavert
(74) *Attorney, Agent, or Firm* — Oppedahl Patent Law Firm LLC

(57) ABSTRACT

A charge pump is provided in the same integrated circuit chip as a control means which permits selectively connecting any of one or more electrodes with conductors along a lead. The charge pump derives about two volts from a one-volt supply, and becomes stable within a few tens of microseconds. The charge pump may be composed of three doublers—the first generating timing signals for the second and third doublers, with the second and third doublers working out of phase with each other.

10 Claims, 6 Drawing Sheets

U.S. PATENT DOCUMENTS

| | | |
|---|---|---|
| 4,815,472 A | 3/1989 | Wise et al. |
| 4,877,032 A | 10/1989 | Heinze et al. |
| 4,878,898 A | 11/1989 | Griffen et al. |
| 4,881,410 A | 11/1989 | Wise et al. |
| 4,902,273 A | 2/1990 | Choy et al. |
| 5,004,275 A | 4/1991 | Miller |
| 5,005,613 A | 4/1991 | Stanley |
| 5,035,246 A | 7/1991 | Heuvelmans et al. |
| 5,072,737 A | 12/1991 | Goulding |
| 5,111,816 A | 5/1992 | Pless et al. |
| 5,113,868 A | 5/1992 | Wise et al. |
| 5,119,852 A | 6/1992 | Von Benda |
| 5,156,154 A | 10/1992 | Valenta, Jr. et al. |
| 5,158,536 A | 10/1992 | Sekins et al. |
| 5,176,619 A | 1/1993 | Segalowitz |
| 5,188,106 A | 2/1993 | Nappholz et al. |
| 5,209,238 A | 5/1993 | Sundhar |
| 5,213,098 A | 5/1993 | Bennett et al. |
| 5,243,981 A | 9/1993 | Hudrlik |
| 5,285,744 A | 2/1994 | Grantham et al. |
| 5,304,208 A | 4/1994 | Inguaggiato et al. |
| 5,305,745 A | 4/1994 | Zacouto |
| 5,313,020 A | 5/1994 | Sackett |
| 5,318,591 A | 6/1994 | Causey, III et al. |
| 5,391,199 A | 2/1995 | Ben-Haim |
| 5,411,532 A | 5/1995 | Mortazavi |
| 5,411,537 A | 5/1995 | Munshi et al. |
| 5,417,717 A | 5/1995 | Salo et al. |
| 5,419,757 A | 5/1995 | Daneshvar |
| 5,423,323 A | 6/1995 | Orth |
| 5,433,198 A | 7/1995 | Desai |
| 5,476,485 A | 12/1995 | Weinberg et al. |
| 5,487,752 A | 1/1996 | Salo et al. |
| 5,490,323 A | 2/1996 | Thacker et al. |
| 5,509,411 A | 4/1996 | Littmann et al. |
| 5,535,752 A | 7/1996 | Halperin et al. |
| 5,544,656 A | 8/1996 | Pitsillides et al. |
| 5,549,650 A | 8/1996 | Bornzin et al. |
| 5,579,234 A | 11/1996 | Wiley et al. |
| 5,579,764 A | 12/1996 | Goldreyer |
| 5,591,142 A | 1/1997 | Van Erp |
| 5,593,460 A | 1/1997 | Lessard |
| 5,628,777 A | 5/1997 | Moberg et al. |
| 5,662,587 A | 9/1997 | Grundfest et al. |
| 5,674,258 A | 10/1997 | Henschel et al. |
| 5,676,153 A | 10/1997 | Smith et al. |
| 5,683,429 A | 11/1997 | Mehra |
| 5,713,937 A | 2/1998 | Nappholz et al. |
| 5,720,768 A | 2/1998 | Verboven-Nelissen |
| 5,743,267 A | 4/1998 | Nikolic et al. |
| 5,751,050 A | 5/1998 | Ishikawa et al. |
| 5,755,759 A | 5/1998 | Cogan |
| 5,788,647 A | 8/1998 | Eggers |
| 5,797,903 A | 8/1998 | Swanson et al. |
| 5,800,460 A | 9/1998 | Powers et al. |
| 5,800,465 A | 9/1998 | Thompson et al. |
| 5,810,735 A | 9/1998 | Halperin et al. |
| 5,814,089 A | 9/1998 | Stokes et al. |
| 5,836,987 A | 11/1998 | Baumann et al. |
| 5,860,964 A | 1/1999 | Willekens et al. |
| 5,902,234 A | 5/1999 | Webb |
| 5,902,248 A | 5/1999 | Millar et al. |
| 5,913,814 A | 6/1999 | Zantos |
| 5,924,997 A | 7/1999 | Campbell |
| 5,935,084 A | 8/1999 | Southworth |
| 5,941,904 A | 8/1999 | Johnston et al. |
| 5,957,957 A | 9/1999 | Sheldon |
| 5,991,661 A | 11/1999 | Park et al. |
| 5,999,848 A | 12/1999 | Gord et al. |
| 5,999,849 A | 12/1999 | Gord et al. |
| 6,002,963 A | 12/1999 | Mouchawar et al. |
| 6,004,269 A | 12/1999 | Crowley et al. |
| 6,009,349 A | 12/1999 | Mouchawar et al. |
| 6,015,386 A | 1/2000 | Kensey et al. |
| 6,024,704 A | 2/2000 | Meador et al. |
| 6,033,398 A | 3/2000 | Farley et al. |
| 6,038,480 A | 3/2000 | Hrdlicka et al. |
| 6,044,297 A | 3/2000 | Sheldon et al. |
| 6,044,299 A | 3/2000 | Nilsson |
| 6,058,329 A | 5/2000 | Salo et al. |
| 6,077,136 A | 6/2000 | Arai et al. |
| 6,078,830 A | 6/2000 | Levin et al. |
| 6,081,748 A | 6/2000 | Struble et al. |
| 6,083,216 A | 7/2000 | Fischer et al. |
| 6,115,626 A | 9/2000 | Whayne et al. |
| 6,115,636 A | 9/2000 | Ryan |
| 6,120,442 A | 9/2000 | Hickey |
| 6,141,588 A | 10/2000 | Cox et al. |
| 6,141,593 A | 10/2000 | Patag |
| 6,155,267 A | 12/2000 | Nelson |
| 6,163,716 A | 12/2000 | Edwards et al. |
| 6,165,135 A | 12/2000 | Neff |
| 6,171,252 B1 | 1/2001 | Roberts |
| 6,197,021 B1 | 3/2001 | Panescu et al. |
| 6,197,677 B1 | 3/2001 | Lee et al. |
| 6,206,835 B1 | 3/2001 | Spillman, Jr. et al. |
| 6,206,874 B1 | 3/2001 | Ubby et al. |
| 6,214,032 B1 | 4/2001 | Loeb et al. |
| 6,223,080 B1 * | 4/2001 | Thompson .................... 607/16 |
| 6,234,973 B1 | 5/2001 | Meador et al. |
| 6,264,606 B1 | 7/2001 | Ekwall et al. |
| 6,277,078 B1 | 8/2001 | Porat et al. |
| 6,287,256 B1 | 9/2001 | Park et al. |
| 6,289,250 B1 | 9/2001 | Tsuboi et al. |
| 6,299,582 B1 | 10/2001 | Brockway et al. |
| 6,301,500 B1 | 10/2001 | Van Herk et al. |
| 6,309,350 B1 | 10/2001 | VanTassel et al. |
| 6,309,385 B1 | 10/2001 | Simpson |
| 6,328,699 B1 | 12/2001 | Eigler et al. |
| 6,360,123 B1 | 3/2002 | Kimchi et al. |
| 6,363,279 B1 | 3/2002 | Ben-Haim et al. |
| 6,366,811 B1 | 4/2002 | Carlson |
| 6,370,431 B1 | 4/2002 | Stoop et al. |
| 6,406,677 B1 | 6/2002 | Carter et al. |
| 6,418,348 B1 | 7/2002 | Witte |
| 6,421,567 B1 | 7/2002 | Witte |
| 6,438,408 B1 | 8/2002 | Mulligan et al. |
| 6,466,820 B1 | 10/2002 | Juran et al. |
| 6,473,638 B2 | 10/2002 | Ferek-Petric |
| 6,473,653 B1 | 10/2002 | Schallhorn et al. |
| 6,477,395 B2 | 11/2002 | Schulman et al. |
| 6,477,417 B1 | 11/2002 | Levine |
| 6,484,057 B2 | 11/2002 | Ideker et al. |
| 6,484,727 B1 | 11/2002 | Vaska et al. |
| 6,496,730 B1 | 12/2002 | Juran et al. |
| 6,580,946 B2 | 6/2003 | Struble |
| 6,584,362 B1 | 6/2003 | Scheiner et al. |
| 6,611,714 B1 | 8/2003 | Mo |
| 6,625,493 B2 | 9/2003 | Kroll et al. |
| 6,628,989 B1 | 9/2003 | Penner et al. |
| 6,643,546 B2 | 11/2003 | Mathis et al. |
| 6,666,826 B2 | 12/2003 | Salo et al. |
| 6,728,562 B1 | 4/2004 | Budd et al. |
| 6,812,796 B2 | 11/2004 | Pryanishnikov et al. |
| 6,885,889 B2 | 4/2005 | Chinchoy |
| 6,934,584 B1 | 8/2005 | Wong et al. |
| 6,957,107 B2 | 10/2005 | Rogers et al. |
| 6,978,184 B1 | 12/2005 | Marcus et al. |
| 6,994,676 B2 | 2/2006 | Mulligan et al. |
| 7,200,437 B1 | 4/2007 | Nabutovsky et al. |
| 7,200,439 B2 | 4/2007 | Zdeblick et al. |
| 7,204,798 B2 | 4/2007 | Zdeblick et al. |
| 7,214,189 B2 | 5/2007 | Zdeblick |
| 7,267,649 B2 | 9/2007 | Zdeblick et al. |
| 7,270,669 B1 | 9/2007 | Sra |
| 7,294,334 B1 | 11/2007 | Michal et al. |
| 7,591,792 B2 | 9/2009 | Bouton |
| 7,892,675 B1 | 2/2011 | Tsukamoto |
| 2001/0002924 A1 | 6/2001 | Tajima |
| 2001/0047138 A1 | 11/2001 | Kokate et al. |
| 2001/0053882 A1 | 12/2001 | Haddock et al. |
| 2002/0026183 A1 | 2/2002 | Simpson |
| 2002/0040236 A1 | 4/2002 | Lau et al. |
| 2002/0045921 A1 | 4/2002 | Wolinsky et al. |
| 2002/0077568 A1 | 6/2002 | Haddock |
| 2002/0077673 A1 | 6/2002 | Penner et al. |
| 2002/0095196 A1 | 7/2002 | Linberg |

| | | |
|---|---|---|
| 2002/0099430 A1 | 7/2002 | Verness |
| 2002/0111560 A1 | 8/2002 | Kokate et al. |
| 2002/0120186 A1 | 8/2002 | Keimel |
| 2002/0151816 A1 | 10/2002 | Rich et al. |
| 2002/0156417 A1 | 10/2002 | Rich et al. |
| 2002/0161307 A1 | 10/2002 | Yu et al. |
| 2002/0169445 A1 | 11/2002 | Jain et al. |
| 2003/0036773 A1 | 2/2003 | Whitehurst et al. |
| 2003/0045920 A1 | 3/2003 | Belden et al. |
| 2003/0065364 A1 | 4/2003 | Wellman et al. |
| 2003/0078623 A1 | 4/2003 | Weinberg et al. |
| 2003/0105496 A1 | 6/2003 | Yu et al. |
| 2003/0135248 A1 | 7/2003 | Stypulkowski |
| 2003/0153952 A1 | 8/2003 | Auricchio et al. |
| 2003/0191502 A1 | 10/2003 | Sharma et al. |
| 2003/0204233 A1 | 10/2003 | Laske et al. |
| 2003/0216800 A1 | 11/2003 | Ebert et al. |
| 2004/0044368 A1 | 3/2004 | Prinzen et al. |
| 2004/0097965 A1 | 5/2004 | Gardeski et al. |
| 2004/0143154 A1 | 7/2004 | Lau et al. |
| 2004/0161528 A1 | 8/2004 | Martinez et al. |
| 2004/0193021 A1 | 9/2004 | Zdeblick et al. |
| 2004/0215049 A1 | 10/2004 | Zdeblick et al. |
| 2004/0220637 A1 | 11/2004 | Zdeblick et al. |
| 2004/0254483 A1 | 12/2004 | Zdeblick et al. |
| 2004/0260346 A1 | 12/2004 | Overall et al. |
| 2005/0027320 A1 | 2/2005 | Nehls et al. |
| 2005/0054892 A1 | 3/2005 | Lau et al. |
| 2005/0075677 A1* | 4/2005 | Ganion et al. ............ 607/9 |
| 2005/0075683 A1 | 4/2005 | Miesel et al. |
| 2005/0102011 A1 | 5/2005 | Lau et al. |
| 2006/0035147 A1 | 2/2006 | Lam et al. |
| 2006/0058588 A1* | 3/2006 | Zdeblick ............ 600/300 |
| 2006/0161211 A1 | 7/2006 | Thompson et al. |
| 2006/0170486 A1* | 8/2006 | Tranchina et al. ......... 327/536 |
| 2006/0264775 A1 | 11/2006 | Mills et al. |
| 2007/0123944 A1 | 5/2007 | Zdeblick |
| 2007/0135721 A1 | 6/2007 | Zdeblick |
| 2007/0161914 A1 | 7/2007 | Zdeblick et al. |
| 2007/0173896 A1 | 7/2007 | Zdeblick |
| 2007/0173897 A1 | 7/2007 | Zdeblick |
| 2007/0179569 A1 | 8/2007 | Zdeblick |
| 2007/0185549 A1 | 8/2007 | Zdeblick |
| 2007/0203517 A1 | 8/2007 | Williams et al. |
| 2007/0219591 A1 | 9/2007 | Zdeblick et al. |
| 2007/0255460 A1 | 11/2007 | Lopata |
| 2008/0007186 A1 | 1/2008 | Lu et al. |
| 2008/0027289 A1 | 1/2008 | Zdeblick |
| 2008/0039916 A1 | 2/2008 | Colliou et al. |
| 2008/0058656 A1 | 3/2008 | Costello et al. |
| 2008/0097227 A1 | 4/2008 | Zdeblick et al. |
| 2008/0097566 A1 | 4/2008 | Colliou |
| 2008/0114230 A1 | 5/2008 | Addis |
| 2008/0140162 A1 | 6/2008 | Goetz et al. |
| 2008/0147168 A1 | 6/2008 | Ransbury et al. |
| 2008/0167702 A1 | 7/2008 | Ransbury et al. |
| 2008/0200802 A1 | 8/2008 | Bhavaraju et al. |
| 2008/0234588 A1 | 9/2008 | Feldman et al. |
| 2008/0255647 A1 | 10/2008 | Jensen et al. |
| 2008/0294218 A1 | 11/2008 | Savage et al. |
| 2008/0306394 A1 | 12/2008 | Zdeblick et al. |
| 2009/0054946 A1 | 2/2009 | Sommer et al. |
| 2009/0054947 A1 | 2/2009 | Bourn et al. |
| 2009/0088811 A1 | 4/2009 | Wulfman |
| 2009/0149902 A1 | 6/2009 | Kumar et al. |
| 2009/0299447 A1 | 12/2009 | Jensen et al. |
| 2010/0030294 A1 | 2/2010 | Wong et al. |
| 2010/0204766 A1 | 8/2010 | Zdeblick et al. |
| 2011/0208067 A1 | 8/2011 | Edman et al. |
| 2011/0224578 A1 | 9/2011 | Edman et al. |

FOREIGN PATENT DOCUMENTS

| | | |
|---|---|---|
| EP | 1136033 | 9/2001 |
| EP | 1266606 | 12/2002 |
| FR | 2097337 | 3/1972 |
| JP | 64056031 | 3/1989 |
| JP | 3-055032 | 3/1991 |
| JP | 5269136 | 10/1993 |
| JP | 6501177 | 2/1994 |
| JP | 6-506619 | 7/1994 |
| JP | 6506619 | 7/1994 |
| JP | 7-542 | 1/1995 |
| JP | 2000139833 | 5/2000 |
| JP | 2000350705 | 12/2000 |
| JP | 2002272758 | 9/2002 |
| JP | 2-99036 | 4/2010 |
| WO | WO9912607 | 3/1999 |
| WO | WO9913561 | 3/1999 |
| WO | WO9913574 | 3/1999 |
| WO | WO0009206 | 2/2000 |
| WO | 0143821 | 6/2001 |
| WO | 0195787 | 12/2001 |
| WO | 02053228 | 7/2002 |
| WO | 02065894 | 8/2002 |
| WO | 2004052182 | 6/2004 |
| WO | 2004066814 | 8/2004 |
| WO | 2004066817 | 8/2004 |
| WO | 2004066825 | 8/2004 |
| WO | 2004067081 | 8/2004 |
| WO | WO2005118064 | 12/2005 |
| WO | 2006029090 | 3/2006 |
| WO | 2006042039 | 4/2006 |
| WO | 2006069322 | 6/2006 |
| WO | 2006069323 | 6/2006 |
| WO | 2006105474 | 10/2006 |
| WO | 2007005641 | 1/2007 |
| WO | 2007075974 | 7/2007 |
| WO | 2007120884 | 10/2007 |
| WO | 2007149546 | 12/2007 |

OTHER PUBLICATIONS

U.S. Appl. No. 12/097,959, filed on Nov. 17, 2008 (Specification, Claims, Abstract and Figures as filed); Zdeblick et al., (2008) "Implantable Integrated Circuit" 199pp.

U.S. Appl. No. 12/395,538, filed on Feb. 27, 2009 (Specification, Claims, Abstract and Figures as filed); Bi et al., (2009) "Integrated Circuit Implementation and Fault Control System, Device, and Method" 163pp.

Auricchio et al., "THe Pacing Therapies for Congestive Heart Failure (PATH-CHF) Study: Rationale, Design, and Endpoints of a Prospective Randomized Multicenter Study", The American Journal of Cardiology, vol. 83(5B) (1999) pp. 130D-135D.

Borky et al., "Integrated Signal Conditioning for Silicon Pressure Sensors", IEEE Transactions on Electron Devices, vol. ED-26, No. 12, Dec. 1979, pp. 1906-1910.

Kovacs, "Technology Development for a Chronic Neural Interface", A dissertation, Stanford University, Aug. 1990, pp. 9, 225-234, 257, 276.

Little et al., "The Output of the Heart and its Control", Physiology of the Heart and Circulation, 4th ed., 1989 Year Book Medical Publishers Inc., pp. 165-187.

Paolocci et al., "Positive inotropic and lusitropic effects of HNP/NO- in Failing Hearts: Independence from β-adrenergic signaling", PNAS, vol. 100, No. 9, Apr. 2003 pp. 5537-5542.

Receveur et al., "Laterally Moving Bi-Stable MEMS DC-Switch for Biomedical Applications", Medtronic Bakken Research Center, The Netherlands (2004), pp. 854-856.

U.S. Appl. No. 11/917,992, filed Jul. 13, 2009 (Specification, Claims, Abstract and Figures as filed); Jensen et al., (2009) "Deployable Epicardial Electrode and Sensor Array" 69pp.

U.S. Appl. No. 12/097,959, filed Nov. 17, 2008 (Specification, Claims, Abstract and Figures as filed); Zdeblick et al., (2008) "Implantable Integrated Circuit" 199pp.

U.S. Appl. No. 12/395,538, filed Feb. 27, 2009 (Specification, Claims, Abstract and Figures as filed); Bi et al., (2009) "Integrated Circuit Implementation and Fault Control System, Device, and Method" 163pp.

Meisel et al., "Transvenous Biventricular Defibrillation", The American Journal of Cardiology, vol. 86 (9A), (Nov. 2000) pp. 76K-85K.

* cited by examiner

METHODS AND APPARATUS FOR LEADS FOR IMPLANTABLE DEVICES

BACKGROUND

It is not easy to make leads for implantable devices that work well when connected with legacy implantable devices, and yet that also offer sophisticated functions such as addressability when used with modern-day implantable devices, and that further offer the flexibility to work with implantable devices not yet devised.

A typical example of an implantable device is a cardiac pacemaker. Other implantable devices include defibrillators, drug delivery systems, neurological stimulators, and bone growth stimulators.

One of the many challenges facing the designer of a lead is the problem that the designer is not permitted to make very many assumptions about the power provided to the lead by the external equipment such as a pacemaker. The power may be of very limited voltage, perhaps as little as one volt. Yet the main circuitry of the chip in each satellite of the lead is likely to require about two volts to carry out its tasks.

SUMMARY OF THE INVENTION

A voltage doubler or charge pump is provided in the same integrated circuit chip as a control means which permits selectively connecting any of one or more electrodes with conductors along a lead. The voltage doubler derives about two volts from a one-volt supply, and becomes stable within a few tens of microseconds. The voltage doubler may be composed of three doublers—the first generating timing signals for the second and third doublers, with the second and third doublers working out of phase with each other.

DESCRIPTION OF THE DRAWING

The invention will be described with respect to a drawing in several figures, of which.

Where possible, like elements among the figures have been designated with like reference numerals, for convenience of notation.

DETAILED DESCRIPTION

Figure 1:
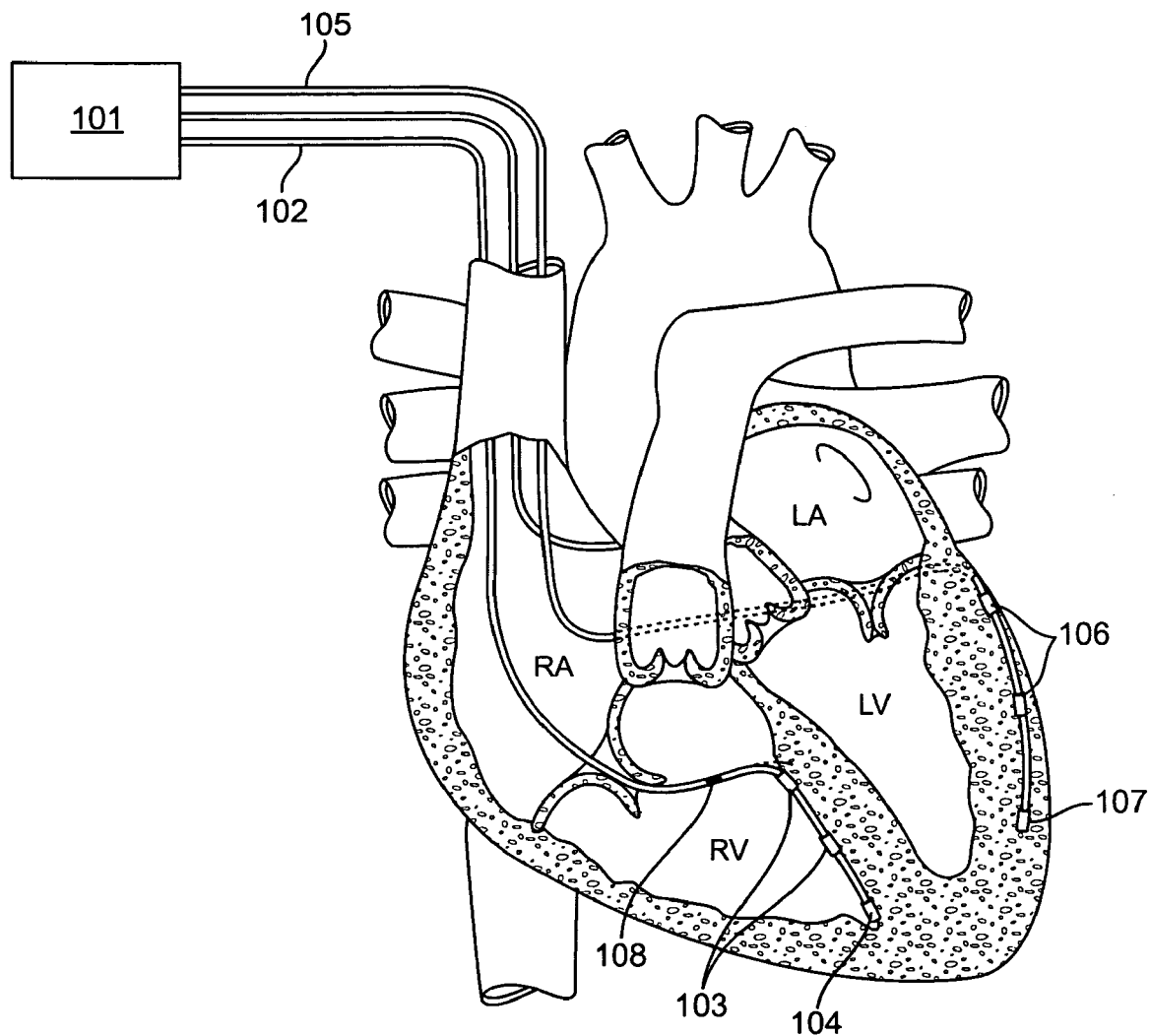
FIG. 1 shows an implantable device 101 and leads including lead 102 implanted in a human heart.

An implantable pulse generator according to an embodiment of the invention is depicted in FIG. 1. FIG. 1 illustrates locations of a number of pacing satellites incorporated in multi-electrode pacing leads, in accordance with an embodiment of the present invention. A pacing and signal detection system 101 provides extra-cardiac communication and control elements for the overall system. In some embodiments, pacing and signal detection system 101 may be, for example, a pacing can of a pacemaker residing in an external or extra-corporeal location.

Right ventricular lead 102 emerges from pacing and signal detection system 101 and travels from a subcutaneous location from pacing and signal detection system 101 into the patient's body (e.g., preferably, a subclavian venous access), and through the superior vena cava into the right atrium. From the right atrium, right ventricle lead 102 is threaded through the tricuspid valve to a location along the walls of the right ventricle. The distal portion of right ventricular lead 102 is preferably located along the intra-ventricular septum, terminating with a fixation in the right ventricular apex. Right ventricular lead 102 includes satellites positioned at locations 103 and 104.

The number of satellites in ventricular lead 102 is not limited, and may be more or less than the number of satellites shown in FIG. 1.

Similarly, left ventricular lead 105 emerges from the pacing and signal detection system 101, following substantially the same route as right ventricular lead 102 (e.g., through the subclavian venous access and the superior vena cava into the right atrium). In the right atrium, left ventricular lead 105 is threaded through the coronary sinus around the posterior wall of the heart in a cardiac vein draining into the coronary sinus. Left ventricular lead 105 is provided laterally along the walls of the left ventricle, which is likely to be an advantageous position for bi-ventricular pacing. FIG. 1 shows satellites positioned at locations 106 and 107 along left ventricular lead 105. Right ventricular lead 102 may optionally be provided with pressure sensor 108 in the right ventricle. A signal multiplexing arrangement allows a lead to include such active devices (e.g., pressure sensor 108) for pacing and signal collection purposes (e.g., right ventricular lead 102). Pacing and signal detection system 101 communicates with each of the satellites at locations 103, 104, 106 and 107. The electrodes controlled by the satellites may also be used to detect cardiac depolarization signals. Additionally, other types of sensors, such as an accelerometer, strain gauge, angle gauge, temperature sensor, can be included in any of the leads.

In the above system, the device components can be connected by a multiplex system (e.g., as described U.S. Pat. No. 7,214,189, U.S. patent application Ser. No. 10/734,490 published as 20040193021 (pending), U.S. patent application Ser. No. 11/793,904 published as 20080255647 (pending) and U.S. patent application Ser. No. 11/794,016 published as 20080312726 (pending); the disclosures of which are herein incorporated by reference), to the proximal end of electrode lead 105 The proximal end of electrode lead 105 connects to a pacemaker 101, e.g., via an IS-1 connector.

During certain embodiments of use, the electrode lead 105 is placed in the heart using standard cardiac lead placement devices which include introducers, guide catheters, guidewires, and/or stylets. Briefly, an introducer is placed into the clavicle vein. A guide catheter is placed through the introducer and used to locate the coronary sinus in the right atrium. A guidewire is then used to locate a left ventricle cardiac vein. The electrode lead 105 is slid over the guidewire into the left ventricle cardiac vein and tested until an optimal location for CRT is found. Once implanted a multi-electrode lead 105 still allows for continuous readjustments of the optimal electrode location. The electrode lead 102 is placed in the right ventricle of the heart. In this view, the electrode lead 102 is provided with one or multiple electrodes 103, 104.

Electrode lead 102 is placed in the heart in a procedure similar to the typical placement procedures for cardiac right ventricle leads. Electrode lead 102 is placed in the heart using the standard cardiac lead devices which include introducers, guide catheters, guidewires, and/or stylets. Electrode lead 102 is inserted into the clavicle vein, through the superior vena cava, through the right atrium and down into the right ventricle. Electrode lead 102 is positioned under fluoroscopy into the location the clinician has determined is clinically optimal and logistically practical for fixating the electrode lead 102.

Summarizing aspects of the above description, in using the implantable pulse generators of the invention, such methods include implanting an implantable pulse generator e.g., as described above, into a subject; and the implanted pulse generator, e.g., to pace the heart of the subject, to perform cardiac resynchronization therapy in the subject, etc. The description of the present invention is provided herein in certain instances with reference to a subject or patient. As used herein, the terms "subject" and "patient" refer to a living entity such as an animal. In certain embodiments, the animals are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the subjects, e.g., patients, are humans.

During operation, use of the implantable pulse generator may include activating at least one of the electrodes of the pulse generator to deliver electrical energy to the subject, where the activation may be selective, such as where the method includes first determining which of the electrodes of the pulse generator to activate and then activating the electrode. Methods of using an IPG, e.g., for pacing and CRT, are disclosed in U.S. Pat. No. 7,214,189 entitled "Methods and apparatus for tissue activation and monitoring"; US publication number US 2008-0255647 entitled "Implantable addressable segmented electrodes" (pending); PCT publication number WO 2006/069323 entitled "Implantable hermetically sealed structures" (pending); international patent publication number WO 2007/075974 entitled "Implantable integrated circuit" (pending); and US patent publication US 2008-0077186 entitled "High phrenic, low capture threshold pacing devices and methods" (pending); the disclosures of the various methods of operation of these applications being herein incorporated by reference and applicable for use with the present devices.

Figure 2:
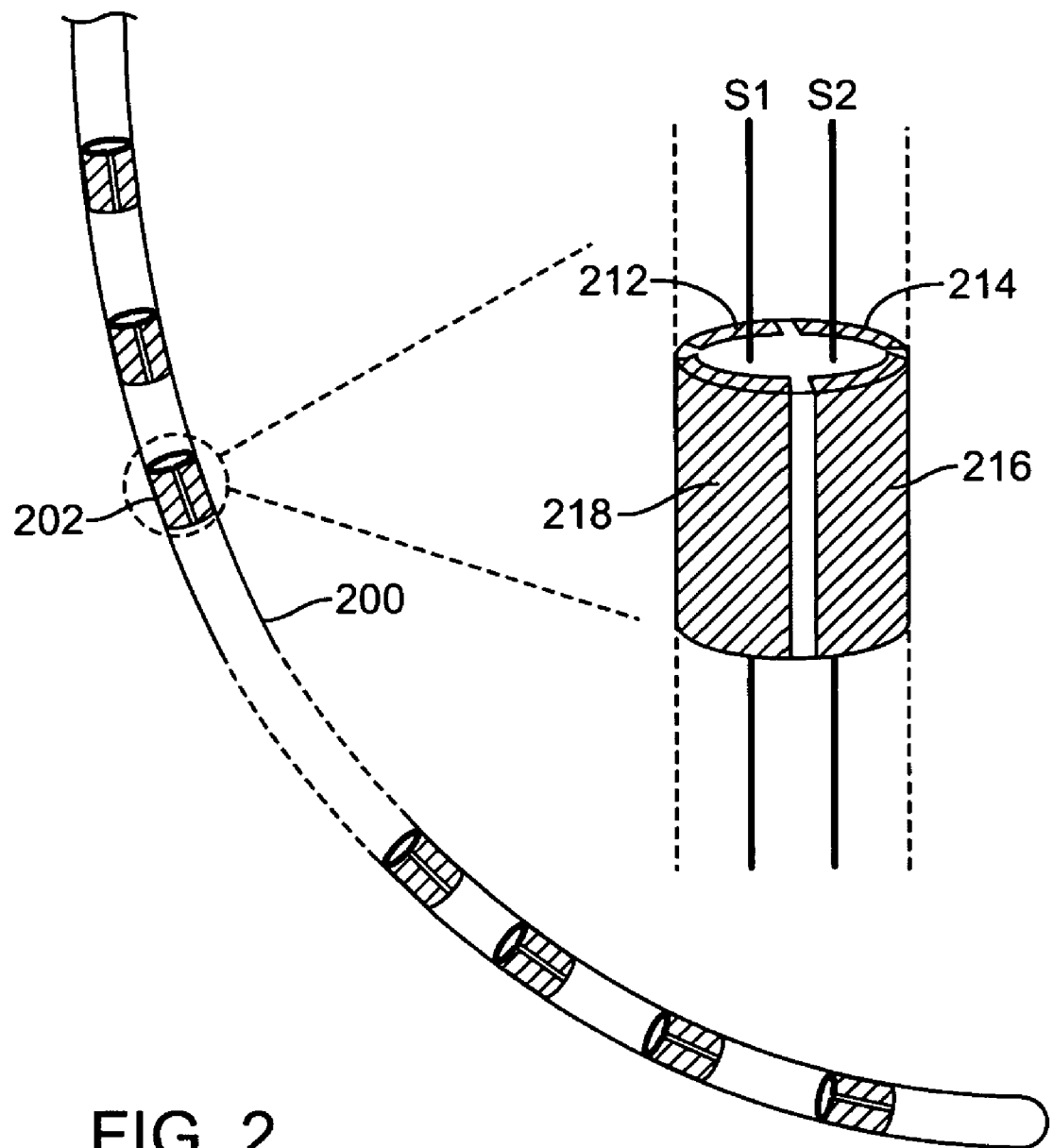
FIG. 2 shows a lead 200 of a type employed in FIG. 1, having satellites 202.

FIG. 2 is an external view of a number of exemplary pacing satellites, in accordance with a multiplex lead embodiment of the present invention. According to one embodiment, a pacing lead 200 (e.g., right ventricular lead 102 or left ventricular lead 105 of FIG. 1) accommodates two bus wires S1 and S2, which are coupled to a number (e.g., eight) of satellites, such as satellite 202. S2, in an exemplary embodiment, is an anode conductor, and 51 is a cathode conductor. FIG. 2 also shows satellite 202 with an enlarged view. Satellite 202 includes electrodes 212, 214, 216, and 218, located in the four quadrants of the cylindrical outer walls of satellite 202 and supported by a support structure of the invention. Each satellite also contains a control chip inside the structure which communicates with a pacing and signal-detection system to receive configuration signals that determine which of the four electrodes is to be coupled to bus wires S1 or S2.

The configuration signals, the subsequent pacing pulse signals, and the analog signals collected by the electrodes can all be communicated through bus wires S1 and S2, in either direction. Although shown in a symmetrical arrangement, electrodes 212, 214, 216 and 218 may be offset along lead 200 to minimize capacitive coupling among these electrodes. The quadrant arrangement of electrodes allows administering pacing current via electrodes oriented at a preferred direction, for example, away from nerves, or facing an electrode configured to sink the pacing current. Such precise pacing allows low-power pacing and minimal tissue damage caused by the pacing signal.

The leads may further include a variety of different effector elements, which elements may employ the satellites or structures distinct from the satellites. The effectors may be intended for collecting data, such as but not limited to pressure data, volume data, dimension data, temperature data, oxygen or carbon dioxide concentration data, hematocrit data, electrical conductivity data, electrical potential data, pH data, chemical data, blood flow rate data, thermal conductivity data, optical property data, cross-sectional area data, viscosity data, radiation data and the like. As such, the effectors may be sensors, e.g., temperature sensors, accelerometers, ultrasound transmitters or receivers, voltage sensors, potential sensors, current sensors, etc. Alternatively, the effectors may be intended for actuation or intervention, such as providing an electrical current or voltage, setting an electrical potential, heating a substance or area, inducing a pressure change, releasing or capturing a material or substance, emitting light, emitting sonic or ultrasound energy, emitting radiation and the like.

Effectors of interest include, but are not limited to, those effectors described in the following applications by at least some of the inventors of the present application: U.S. Patent publication number US 20040193021 entitled "Method And System For Monitoring And Treating Hemodynamic Parameters" (pending); U.S. Patent publication number US 20060058588 entitled "Methods And Apparatus For Tissue Activation And Monitoring" (patented with issue no. of 7,214,189); International patent publication number WO 2006/069323 (pending); U.S. Patent publication no. US 2006-0161211 entitled "Implantable Accelerometer-Based Cardiac Wall Position Detector" (pending); U.S. Pat. No. 7,200,439 entitled "Method and Apparatus for Enhancing Cardiac Pacing"; U.S. Pat. No. 7,204,798 entitled "Methods and Systems for Measuring Cardiac Parameters"; U.S. Pat. No. 7,267,649 entitled "Method and System for Remote Hemodynamic Monitoring"; U.S. patent publication no. US 2006-0217793 entitled "Fiberoptic Tissue Motion Sensor" (patented with issue no. of 7,837,634); U.S. Pat. No. 7,028,550 entitled "Implantable Pressure Sensors"; U.S. Patent publication No. US 2006-0116581 entitled "Implantable Doppler Tomography System" (patented with issue no. of 7,925,329); and US patent publication US 2008-0255629 (pending) entitled "Cardiac Motion Characterization by Strain Measurement". These applications are incorporated in their entirety by reference herein.

Figure 3:
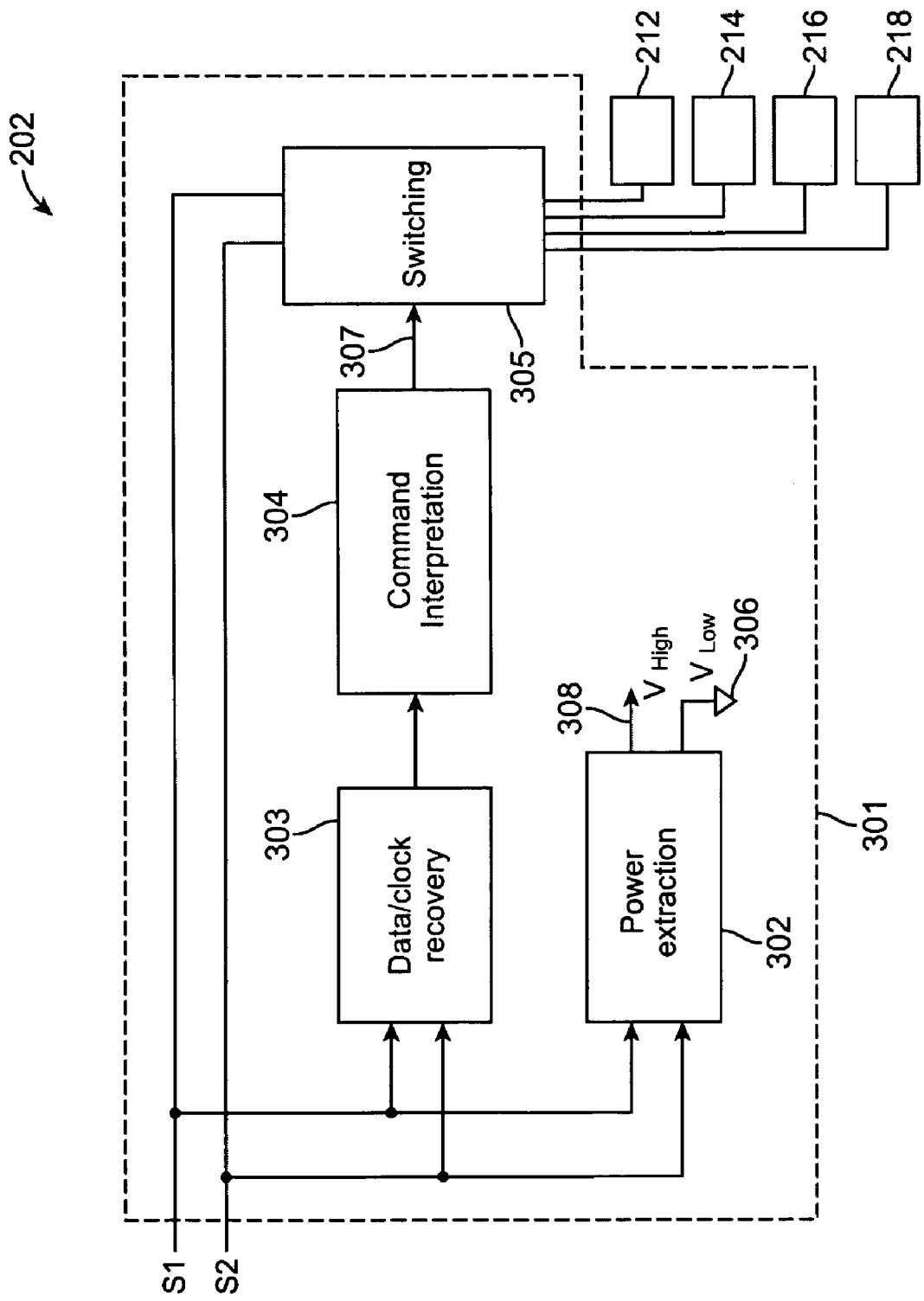
FIG. 3 is a functional block diagram of a satellite 202 as shown in FIG. 2.

A typical satellite 202 (shown in FIG. 2) is shown in more detail in FIG. 3. Conductors S1, S2 are shown, connecting with an IC (integrated circuit) 301, which is a six-terminal device. The other four terminals are connection points to electrodes 212, 214, 216, and 218 (also visible in FIG. 2).

IC 301 includes a power extraction block 302, a data and clock recovery block 303, a command interpretation block 304, and a switching block 305.

The power extraction block 302 obtains DC power from the conductors S1, S2, and makes the power available for use in other parts of the IC 301, for example as power line Vhigh and ground.

The data and clock recovery block 303 detects a clock signal from conductors S1, S2, and uses the clock signal to time the sampling of the conductors S1, S2 to detect data on the conductors S1, S2. A command interpretation block 304 receives data from the block 303 and picks out commands from the data.

The switching block 305 responds to commands from the command block 304, and selectively connects an electrode 212, 214, 216, 218 with conductor S1 or conductor S2.

Circuitry may also be provided that permits IC 301 to send messages back along conductors S1, S2 to system 101 (FIG. 1).

The data/clock recovery circuitry 303 and the command interpretation circuitry 304 may be the circuitry set forth in international patent publication number WO 2007/075974 or in other patent documents listed above that are incorporated by reference herein.

Default-Mode Operation. In one embodiment, the integrated circuits are configured to be operable in a default mode, e.g., where the circuits are employed in electrode assemblies on a lead, such as a multi-electrode lead (MEL). In such an embodiment, the circuits include a default-mode functional block, which enables the circuit and assembly coupled thereto to operate in a default mode without the electrodes being first powered up and configured. As such, in these embodiments a device configuration provided by said integrated circuit is functional without power being applied to said integrated circuit. This default-mode operation allows an implantable medical device, such as a pacemaker, to operate without consuming extra power for electrode configuration. Furthermore, the default-mode operation allows the MEL to easily interoperate with conventional pacing systems. In such embodiments, the integrated circuit may have a functional block that enables default operation, e.g., as described above.

In certain embodiments, the circuit is configured to have a default configuration connecting one supply terminal to one or more effectors upon power up of said circuit. As such, in these embodiments, upon power up of the circuit, the circuit assumes a default configuration with respect to one or more effectors that are coupled to the circuit, without receiving any configuration data from a remote source.

Discussing this function in greater detail, embodiments of the present invention provide implantable devices, such as satellite units of a multi-electrode lead (MEL) that are operable in a default mode. Such devices include an integrated circuit which is configured such that it is operational upon power up whether or not it receives configuration data following power up. For example, a pacemaker lead of the present invention can operate in a default mode after it is coupled to a pacemaker can, regardless of whether it receives electrode configuration signals from the pacemaker can. In the default mode, a pacemaker lead can provide pacing functions in response to pacing signals that fall within an accepted range. The ranges of signals that are accepted by a pacemaker lead are broad enough to include pacing signals generated by many different models of pacemaker cans. As such, pacemaker leads of the present invention are not limited to being used with only one pacemaker can model or one class of pacemaker cans made by a particular manufacturer.

The present invention provides the ability to replace the preexisting can with one from a wide variety of makes and models, should the need arise. This can be accomplished while using the existing pacemaker leads. This is desirable over performing an additional surgical procedure to replace the preexisting pacemaker leads. It would be desirable if an implanted pacemaker lead could respond to pacing signals generated by one pacemaker model or a class of pacemaker models made by any manufacturer.

Pacemaker leads can include one or more integrated circuit chips. Each of the chips can include a set of switches (e.g., 4 switches). Each of the switches couple or decouple an anode wire or a cathode wire in the lead to an electrode. The switches are typically implemented by a set of transistors according to any convenient circuit design techniques.

A pacemaker lead of the present invention is connected to a pacemaker can. The pacemaker lead is operable in a default mode. In the default mode, the switches in the integrated circuit chips remain in or switch to a default configuration. When the switches are in the default configuration, one or more of the electrodes are coupled to the anode wire and/or the cathode wire. In one approach, the switches in one or more chips can be switched to couple a corresponding electrode to an anode wire or a cathode wire. The switches can also decouple a corresponding electrode from both the anode wire and the cathode wire so that the pacemaker cannot send current to that electrode. Thus, each of the switches can be placed in one of three states: decoupled, coupled to the anode wire, or coupled to the cathode wire.

Figure 9:
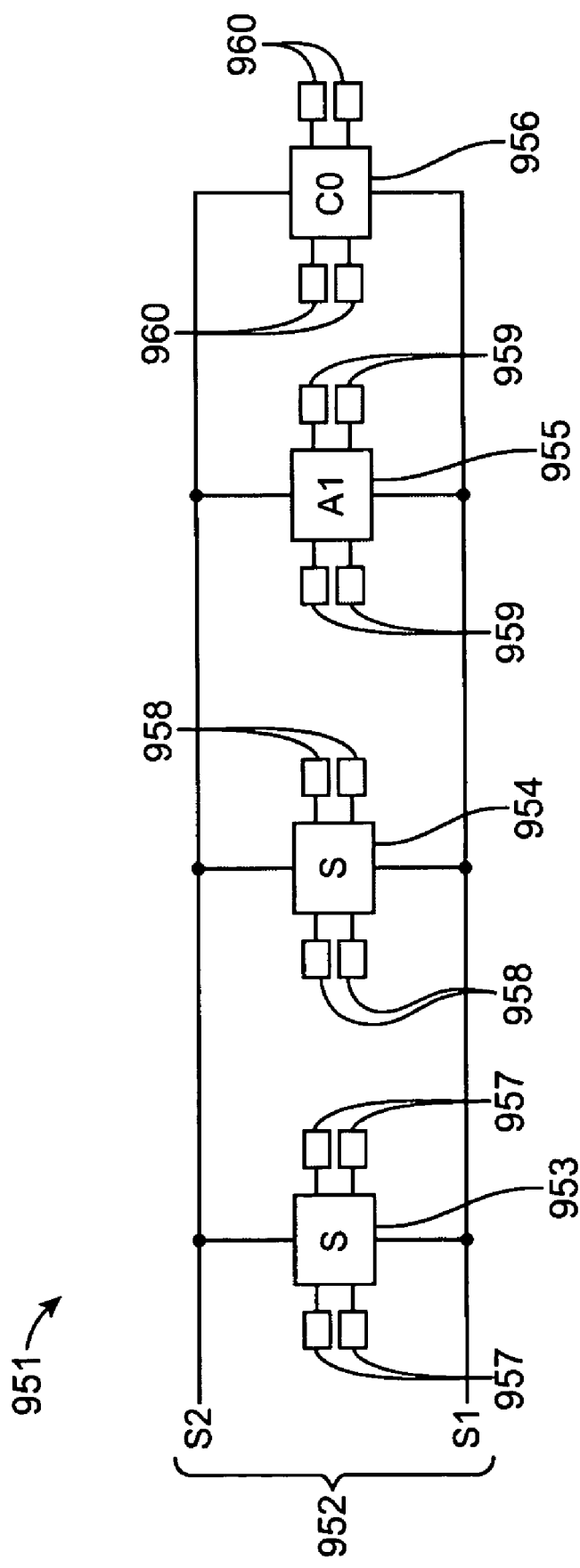
FIG. 9 shows four chips of three different types disposed along a lead.

Turning momentarily to FIG. 9, what is shown is a pacemaker lead 951 which connects to a pacemaker can at end 952. Disposed at the distal end of lead 951 (the end furthest from the end 952) is chip 956. Next is chip 955, then chip 954, and finally chip 953 closest to the pacemaker can. (This example shows four chips and thus four satellites, but other numbers may be employed.)

Each chip is connected to electrodes. For example chip 953 is connected to electrodes 957, chip 954 is connected to electrodes 958, chip 955 is connected to electrodes 959, and chip 956 is connected to electrodes 960.

Within each chip are semiconductor switches (omitted for clarity in FIG. 9) which can selectively connect a particular electrode to conductor S1 or to conductor S2, or can leave the electrode at a high impedance relative to conductors S1 and S2. Each electrode has two such switches (one coupled to S1 and the other coupled to S2), and thus in this embodiment each chip has four electrodes, so that each chip contains eight such switches. In the exemplary embodiment of lead 951, which has four chips, there are thus thirty-two such switches.

In an exemplary embodiment the chips disposed at 953, 954, 955, 956 are not identical in their default function. A first type of chip is a chip which, in default, connects all of its electrodes to the cathode (S1) conductor. A second type of chip, in default, connects all of its electrodes to the anode (S2) conductor. A third type of chip, in default, does not connect its electrodes to either of the conductors.

In the embodiment of FIG. 9, the chip 956 is of the first type (here called "c0") namely with a default connection to the cathode (S1) conductor. The chip 955 is of the second type (here called "a1") namely with a default connection to the anode (S2) conductor. Each of chips 954, 953 is of the third type (here called "s") which in default does not connect its electrodes to either conductor.

With a legacy pacemaker sending a pulse in a single-wire way (using body tissue as a return for a pulse emitted on the S1 conductor) then the only active electrodes 960 are those at the distal satellite.

With a legacy pacemaker sending a pulse in a two-wire way (on conductors S1 and S2) then the active electrodes are those at 959 (coupled with the S2 conductor) and those at 960 (coupled with the S1 conductor).

Some types of pacemaker cans are able to generate configuration signals that can control the states of the switches in the integrated circuit chips that are in an implantable pacemaker lead. These types of pacemaker cans are able to change the states of the switches in order to stimulate any of the electrodes in the lead in any desired pacing configuration.

However, other types of pacemaker cans cannot generate configuration signals for controlling the states of the switches. According to the present invention, one or more of the electrodes are coupled to the anode and/or cathode wire in a default mode. Therefore, a pacemaker can that is not able to generate configuration signals for changing the states of the switches is still able to send current to at least one of the electrodes in a default mode. The default configuration of the switches allows any pacemaker can that is able to generate pacing signals within an accepted range to stimulate the cardiac tissue and provide at least a basic pacing function.

According to some embodiments of the present invention, an implantable pacemaker lead is already in a functional default mode before the lead is coupled to a pacemaker can. According to other embodiments of the present invention, an implantable pacemaker lead enters a functional default mode after the lead is coupled to a pacemaker can, and the power supply voltage reaches or exceeds a predefined threshold voltage. As mentioned above in connection with FIG. 9, the integrated circuit chips on a pacemaker lead can be classified as three types of default mode chips: anode default, cathode default, and off default. Anode default chips contain switches that couple one or more electrodes to the anode wire in default mode. The DC lead impedance for an anode default chip can be, for example, in the range of about 20 to about 225Ω, such as from about 112 to about 225Ω, such as about 120Ω.

Cathode default chips contain switches that couple one or more electrodes to the cathode wire in default mode. The DC lead impedance for a cathode default chip can be, for example, in the range of about 15 to about 80Ω, such as from about 20 to about 80Ω, including about 40Ω. If the pulse amplitudes of the pacing signals are increased, the lead impedances are reduced.

Chips that are off by default contain switches that disconnect all of their electrodes from the anode and cathode wires. Chips that are off by default can be, for example, in the range of about a megohm impedance until turned on using a pacemaker can.

A pacemaker lead of the present invention can have integrated circuit chips with any number of switches that are coupled to a corresponding number of electrodes. For example, in one instance, electrode configuration can be set to provide the patient an effective therapeutic procedure. In another instance, the electrode configuration can be reset to provide the same patient a more effective therapeutic procedure.

Power generation. Returning to FIG. 3, the power extraction or power generation circuitry 302 is shown. conductors S1 and S2 receive power from outside of the chip 301. The power extraction circuitry 302 has the task of developing an appropriate power supply for use within the chip 301, here with conductors 308 and 306 arbitrarily denoted as Vhigh and Vlow respectively.

Electrode switching to S2 conductor. Returning to FIG. 3, the switching circuitry 305 is shown. conductors S1 and S2 receive signals from outside of the chip 301. The switching circuitry 305 provides a tri-state driver for each electrode 212, 214, 216, 218. By "tri-state driver" is meant that a particular electrode might be connected to conductor S1 or to conductor S2 or might be at a high impedance relative to both of conductors S1 and S2 ("floating"). The drivers are controlled by control lines 307 (FIG. 3) from the command interpretation circuitry 304.

Figure 8:
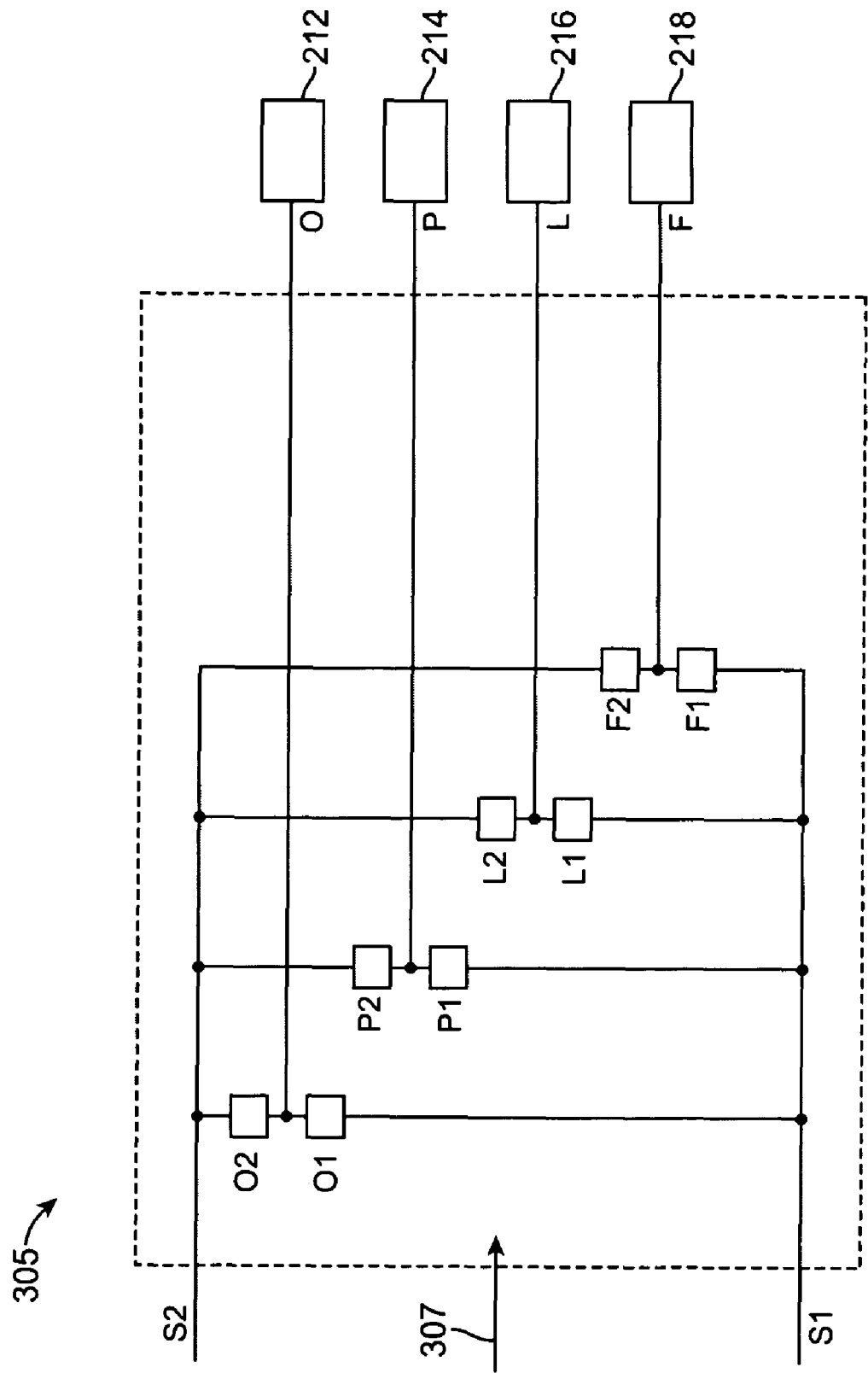
FIG. 8 shows a switching circuitry as might be used in the integrated circuit of the satellite of FIG. 3.

FIG. 8 details a portion of the switching circuitry 305 in a system according to the invention. Electrode 212 is connected by a line O with switches O2 and O1 which together comprise a tri-state driver. Electrode 214 is connected by a line P with switches P2 and P1 which together comprise a tri-state driver. Electrode 216 is connected by a line L with switches L2 and L1 which together comprise a tri-state driver. Finally, electrode 218 is connected by a line F with switches F2 and F1 which together comprise a tri-state driver.

In FIG. 8, each tri-state driver is controlled by control lines 307, the details of which are omitted for clarity in FIG. 8. As with any tri-state driver, it is important that at most one of the switches be "on" at a particular time. Stated differently, it should never happen that both switches are on at the same time. This, for example, switches O2 and O1 should never be simultaneously "on".

Coping with severely limited voltage. One of the many challenges facing the designer of a lead is, as mentioned above, the problem that the designer is not permitted to make very many assumptions about the power provided to the lead by the external equipment such as a pacemaker. The power may be of very limited voltage, perhaps as little as one volt. Yet the main circuitry of the chip in each satellite of the lead is likely to require about two volts to carry out its tasks.

Figure 4:
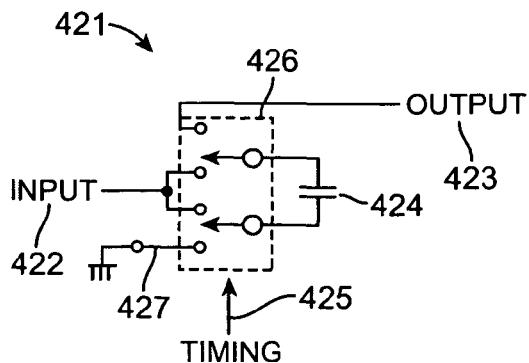
FIG. 4 shows a classic flying-capacitor voltage doubler as is well known in the art.

Turning to FIG. 4, what is seen is a classic flying-capacitor voltage doubler 421 as is well known in the art. A voltage input 422 is provided to the doubler 421. The output 423 is shown. Capacitor 424 is connected by double-pole double-throw switch 426 as will be discussed in some detail. DPDT switch 426 is controlled by timing signal or signals 425.

In a first phase, the switch 426 connects the capacitor 424 between input 422 and ground, with the top of the capacitor connected to the input 422 and the bottom of the capacitor connected to ground. This charges up the capacitor 424.

In a second phase, the switch 426 connects the top of the capacitor to the output 423, and connects the bottom of the capacitor to the input 422.

In this way the voltages are "added up". The voltage at the input (say, 1 volt) is added to the voltage stored in the capacitor (also 1 volt, having been charged during the first phase). The sum, two volts, is delivered to the output 423.

Figure 5:
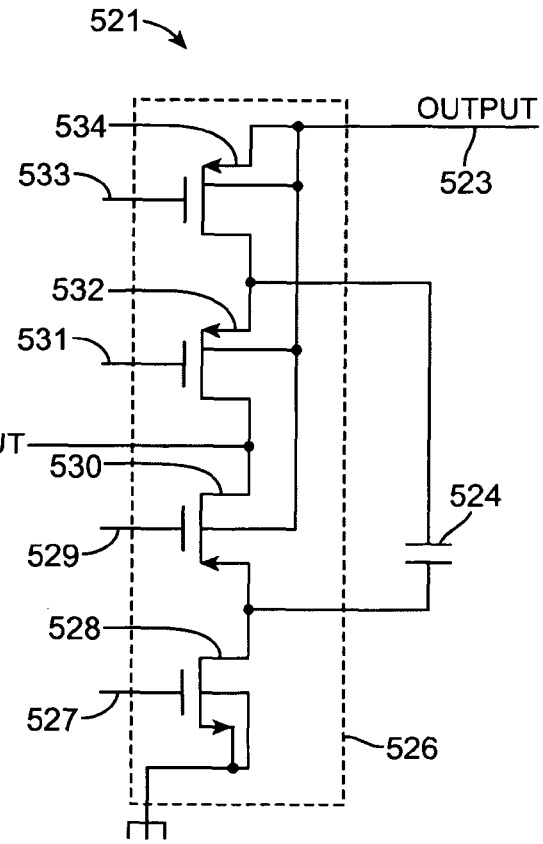
FIG. 5 shows in schematic detail a voltage doubler as employed in the apparatus according to the invention.

FIG. 5 shows in schematic detail a voltage doubler 521 as employed in the apparatus according to the invention. Input 522 may be seen, as well as output 523. Capacitor 524 is shown. Transistor switches 534, 532, 530, and 528 are shown, and they provide the function described in FIG. 4 by switch 426. The transistor switches are turned on and off by timing signals 533, 531, 529, and 527.

In a typical embodiment the timing signals cycle at a megahertz or so. Such a frequency permits minimizing the size of the capacitors 424 (FIG. 4) and 524 (FIG. 5). If much lower frequencies had been used, it would have been necessary to make the capacitors larger, and this is not easy to do in an integrated circuit of limited size such as is being discussed herein.

Figure 6:
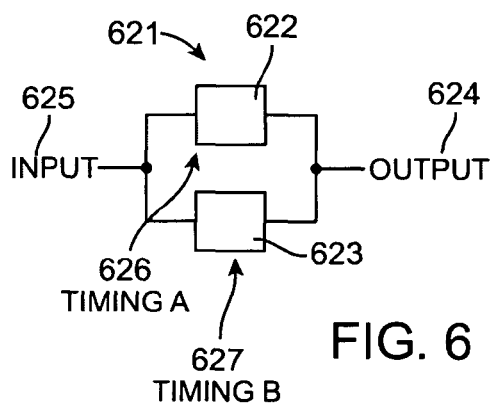
FIG. 6 shows two voltage doublers excited out of phase with each other, so as to provide better power generation.

FIG. 6 shows a composite voltage doubler 621 composed of voltage doublers 622, 623 excited out of phase with each other, so as to provide better power generation. Input 625 and output 624 are shown. Timing signals 626, 627 are provided to the doublers 622 and 623 respectively. The timing signals are, in this embodiment, 180 degrees out of phase with each other. In this way, the two doublers 622 and 623 fill in each others' gaps, providing double the bandwidth of a single doubler 622 or 623 taken alone.

Yet another challenge, as mentioned above, is that the designer of the lead is required to provide fully functioning chips within only a few tens of microseconds of the initial arrival of power at the lead. It turns out that a single voltage doubler (and its associated timing circuitry) cannot reliably "settle" quickly enough into generation of the needed voltage levels.

Figure 7:
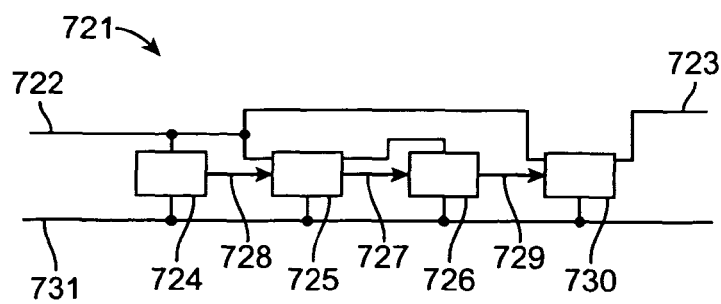
FIG. 7 shows cascaded voltage doublers according to the invention.

FIG. 7 shows cascaded voltage doublers according to the invention. A voltage input 722 is shown, which is provided to first timing circuitry 724, to first doubler 725, and to second doubler 730. First timing circuitry 724 provides timing signals 728 to first doubler 725.

First doubler 725 provides doubled voltage to second timing circuitry 726. Second timing circuitry 726 provides timing signals 729 to second doubler 730. Second doubler 730 has output 723.

First doubler 725, together with first timing circuitry 724, is designed to "settle" very quickly, which it is able to do because it does not need to generate a lot of power. It only needs to generate enough power to give stable operation to second timing circuitry 729 (and it need not generate enough power to power the main functions of the chip).

Second doubler 730, together with second timing circuitry 729, is designed so as to be able to generate enough power to power the main functions of the chip.

In a typical embodiment, the power input 722 might be as small as one volt. First timing circuitry 724 is designed to be able to do its job despite having only one volt powering the circuitry.

The output of the first doubler 725 is nominally two volts, and this permits reliable and stable operation of second timing circuitry 726.

In this way, the composite doubler 721 is able to provide high quality doubled voltage at output 723, all within only a few tens of microseconds of initial supply of as little as one volt.

In an exemplary embodiment, the first doubler 724 may have a flying capacitor of between about 2 and 3 picofarads, for example about 2.7 picofarads. In the exemplary embodiment, the second doubler 724 may have a flying capacitor of between about 13 and 16 picofarads. Other doublers that do not need to generate very much current may each have a flying capacitor of between about 250 femtofarads and about 300 or 500 femtofarads.

As was mentioned above, one of the challenges facing the designer of a lead according to the invention is that it is often necessary to accommodate any of a variety of legacy or more modern implantable devices. Thus while one implantable device may provide around 1 or 1.1 volts, a different implantable device may provide a higher voltage such as 3 volts, which higher voltage makes it unnecessary to make use of voltage doublers at all.

This it may be described that the doubler is only needed if the input voltage is low. If the input voltage is sufficiently high, then it might be advantageous to bypass or disable the doubler or doublers to prevent an excessively high output voltage from damaging the other internal parts of the integrated circuit. A threshold for bypassing the doubler or doublers might be about 3 volts DC provided at the lead conductor or conductors.

In one exemplary embodiment of the invention, what is described is a lead for use with an implantable device, the lead having at least two satellites at respective distinct positions along its length, the lead having at least two conductors extending along at least part of its length, the conductors extending to and electrically connected to each of the at least two satellites and further extending to an end of the lead for electrical connection to the implantable device. Each satellite comprises at least one respective electrode positioned for contact external to the lead. Each satellite further comprises a respective integrated circuit electrically connected with the at least two conductors and electrically connected with the respective electrode. Each integrated circuit comprises respective first timing circuitry powered from the at least two conductors. Each integrated circuit further comprises a respective first voltage doubler powered from the at least two conductors and switched by the respective first timing circuitry. Each integrated circuit comprises respective second timing circuitry powered from the first voltage doubler. Each integrated circuit further comprises a respective second voltage doubler powered from the at least two conductors and switched by the respective second timing circuitry. Each integrated circuit further comprises a control means controlling connections between the at least one respective electrode and the at least two conductors, the control means powered from the respective second voltage doubler.

There may be a respective third voltage doubler powered from the at least two conductors and switched by the respective second timing circuitry out of phase with respect to the switching of the second voltage doubler, the control means powered from the respective third voltage doubler in addition to the respective second voltage doubler.

The power provided to the control means by the voltage doubler may be about two volts, characterized as being at least 1.8 volts. The power provided to the voltage doubler by the at least two conductors may be about one volt, characterized as being no more than 1.1 volts. The output of the voltage doubler may be stable within about ten or fifteen or twenty microseconds, characterized as being stable within fifty microseconds of the provision of power to the voltage doubler by the at least two conductors.

An exemplary sequence of events is that within each integrated circuit:
  first timing signals are generated drawing upon power from the at least two conductors;
  a voltage is doubled from the at least two conductors, the doubling switched by the respective first timing signals, yielding a first doubled voltage;
  second timing signals are generated drawing upon power from the first voltage doubled voltage;
  a voltage is doubled from the at least two conductors, the doubling switched by the respective second timing signals, yielding a second doubled voltage.

The above discussion addresses a typical case where the lead contains two conductors. It will be appreciated, however, that the teachings of the invention are equally available in the case where a lead has only one conductor, the remainder of the conduction path being through body tissue to a connection point at the implantable device.

The above discussion uses the term "voltage doubler" as a convenient way to describe the approach that is employed to address some of the challenges faced by designers in the area being discussed. The more general term "charge pump" is perhaps a clearer term to describe the approaches set forth for addressing some of the challenges.

Those skilled in the relevant art will have no difficulty whatsoever devising myriad obvious improvements and variants of the apparatus and methods without undue experimentation, all of which improvements and variants are intended to be encompassed within the claims which follow.

The invention claimed is:
1. A lead for use with an implantable device, the lead having at least two satellites formed along with its length, the lead having at least one conductor extending along at least part of its length, the at least one conductor extending to and electrically connected to each of the at least two satellites and further extending to an end of the lead for electrical connection to the implantable device, with each satellite comprising:

at least one electrode positioned for contact external to the lead; and an integrated circuit electrically connected with the at least one conductor and electrically connected with the at least one electrode, the integrated circuit comprising:

a first timing circuitry coupled with the at least one conductor and powered from the at least one conductor;

a first charge pump coupled with the at least one conductor and the first timing circuitry and powered from the at least one conductor and switched by the first timing circuitry;

a second timing circuitry coupled with the first charge pump and powered from the first charge pump;

a second charge pump coupled with the at least one conductor and the second timing circuitry, the second charge pump powered from the at least one conductor and switched by the second timing circuitry;

a third charge pump coupled with the at least one conductor and the second timing circuitry, the third charge pump powered from the at least one conductor and switched by the second timing circuitry out of phase with respect to switching of the second charge pump; and a control means controlling connections between the at least one electrode and the at least one conductor, the control means coupled with the second charge pump and the third charge pump and powered from the second charge pump and the third charge pump.

2. The lead of claim 1, wherein the power provided to the control means by the first charge pump is at least 1.8 volts, and wherein the power provided to the first charge pump by the at least one conductor is no more than 1.1 volts.

3. The lead of claim 1 wherein an output of the first charge pump becomes stable within fifty microseconds from an initial provision of power to the first charge pump by the at least one conductor.

4. The lead of claim 1 wherein the first charge pump is disabled or bypassed when power provided to the first charge pump by the at least one conductor is at least 3 volts.

5. The lead of claim 1 wherein the second charge pump is disabled or bypassed when power provided to the second charge pump by the at least one conductor is at least 3 volts.

6. The lead of claim 1 wherein a number of the at least one conductor is one.

7. The lead of claim 1 wherein a number of the at least one conductor is two.

8. The lead of claim 1 wherein a number of the at least one electrode is at least four.

9. The lead of claim 1 wherein a number of the at least one electrode is at least four.

10. A satellite for use with a lead having at least one conductor, the lead for use with an implantable device, the satellite comprising:

at least one electrode positioned for contact external thereto; and an integrated circuit electrically connected with the at least one conductor and electrically connected with the at least one electrode, the integrated circuit comprising:

a first timing circuitry coupled with the at least one conductor and powered from the at least one conductor;

a first charge pump coupled with the at least one conductor and the first timing circuitry and powered from the at least one conductor and switched by the first timing circuitry;

a second timing circuitry coupled with the first charge pump and powered from the first charge pump;

a second charge pump coupled with the at least one conductor and the second timing circuitry, the second charge pump powered from the at least one conductor and switched by the second timing circuitry;

a third charge pump coupled with the at least one conductor and the second timing circuitry, the third charge pump powered from the at least one conductor and switched by the second timing circuitry out of phase with respect to switching of the second charge pump; and a control means controlling connections between the at least one electrode and the at least one conductor, the control means coupled with the second charge pump and the third charge pump and powered from the second charge pump and the third charge pump.

* * * * *